(12) United States Patent
Pink et al.

(10) Patent No.: US 11,000,469 B1
(45) Date of Patent: May 11, 2021

(54) NAIL GEL BUILDER COMPOSITION

(71) Applicant: Orly International, Inc., Van Nuys, CA (US)

(72) Inventors: Jeff Pink, Beverly Hills, CA (US); Daniel H. Werner, Burbank, CA (US)

(73) Assignee: ORLY INTERNATIONAL, INC., Van Nuys, CA (US)

( * ) Notice: Subject to any disclaimer, the term of this patent is extended or adjusted under 35 U.S.C. 154(b) by 27 days.

(21) Appl. No.: 16/504,245

(22) Filed: Jul. 6, 2019

Related U.S. Application Data

(60) Provisional application No. 62/694,727, filed on Jul. 6, 2018.

(51) Int. Cl.
*A61K 8/04*     (2006.01)
*A61K 8/81*     (2006.01)
*A61Q 3/02*     (2006.01)

(52) U.S. Cl.
CPC ............ *A61K 8/8152* (2013.01); *A61K 8/042* (2013.01); *A61Q 3/02* (2013.01); *A61K 2800/10* (2013.01); *A61K 2800/81* (2013.01)

(58) Field of Classification Search
None
See application file for complete search history.

(56) References Cited

U.S. PATENT DOCUMENTS

| | | |
|---|---|---|
| 6,244,274 B1 | 6/2001 | Sirdesai et al. |
| 8,367,045 B2 | 2/2013 | Raney et al. |
| 9,526,686 B2 | 12/2016 | Haile |
| 9,956,160 B2 | 5/2018 | Luu |
| 2011/0256080 A1 | 10/2011 | Kozachek et al. |
| 2012/0247496 A1 | 10/2012 | Taylor |
| 2014/0234239 A1 | 8/2014 | Sirdesai |
| 2015/0306013 A1 | 10/2015 | Kergosien et al. |
| 2015/0335568 A1 | 11/2015 | Lein |
| 2017/0360683 A1 | 12/2017 | Sheran et al. |
| 2018/0092827 A1 | 4/2018 | Sheran et al. |

FOREIGN PATENT DOCUMENTS

| | | |
|---|---|---|
| CN | 107595669 | 1/2018 |
| JP | 2013099508 | 5/2013 |

*Primary Examiner* — Jessica Worsham
(74) *Attorney, Agent, or Firm* — Shlesinger, Arkwright & Garvey LLP

(57) ABSTRACT

A UV curable gel composition adapted to be applied to a nail with a brush to build and extend the nail comprising one or more acrylate/carbamate copolymer resins, one or more urethane methacrylate oligomers of di-functionality, one or more methacrylate resins, one or more Isophorone Diisocyanate end-capped with Hydroxyethyl Methacrylate resins, one or more ethylenically unsaturated mono functional monomers, a photoinitiator and at least one acid-based adhesion promotor wherein the composition having a viscosity of about 11,000 centipoise to about 14,000 centipoise and a specific gravity of less than about 1.2. The invention includes an applicator kit for the composition and methods of its use.

6 Claims, No Drawings

NAIL GEL BUILDER COMPOSITION

CROSS-REFERENCE TO RELATED APPLICATIONS

This application claims the benefit of priority from U.S. Provisional Application Ser. No. 62/694,727, filed on Jul. 6, 2018, which is incorporated herein by reference.

FIELD OF THE INVENTION

This invention relates to radiation-curable gel compositions for cosmetically extending the length of fingernails and toenails, an application kit for the gel composition and methods of its use.

BACKGROUND OF THE INVENTION

Cosmetically extending the length of a natural nail is well known. A nail form is placed under the leading edge of a nail and a builder composition is coated over the natural nail and the form. The builder composition is cured and additional coatings are applied and cured. After a desired length and thickness is achieved, the form is removed and the nail is shaped by filing. There are two types of builder compositions; acrylic and hard gel.

Acrylic nail builder compositions create good nail length, but are difficult to apply. Mixing of the liquid monomer with the powder polymer must be done in a correct ratio. This can lead to errors and variances in applications. A steep learning curve is associated with acrylic nail builder compositions. Acrylic nail builders are also difficult to remove. Although acrylic nail builders provide superior strength, shaping and filing can be abrasive, the natural nail can be damaged and the filing produces dust and discomfort to the user. Finally, acrylic compositions generate a very strong chemical odor that is undesirable.

Hard gel builders have a relatively low molecular weight and a tighter molecular structure that provides strength and durability. Hard gels excel at creating nail length but are notoriously difficult to apply. Hard gel builders require exactness in the amount of product applied and variances in viscosity make it difficult to control its application therefore skill is required to shape the nail properly. A number of different tools must be used with hard gel builders such as brushes and pots that must be cleaned and sanitized following each use. In addition to the above, hard gels are sticky and messy and the shaping requires the use of abrasive e-files that generate dust and discomfort to a user.

Soft gels are a preferred choice for adding strength to a natural nail without causing damage to the nail. Soft gels are premixed semi-solid monomers and oligomers that, after coating, will harden into polymers when exposed to UV-A light. Soft gels are specifically formulated to provide a higher molecular weight having a more elongated molecular structure. This molecular structure creates space between the crosslinked agents so that a solvent may be used to "soak off" or break down the gel and safely remove it without the need for abrasive filing. Application of a soft gel is relatively easy, requiring little to no training. Soft gels may be cured using UV or LED light and the cured coating is easily shaped without the need for special equipment. However, conventional soft gels lack the strength and durability characteristics provided by a hard gel.

A need has existed in the art for a nail builder having the strength and durability of a hard gel or an acrylic coating but with the application advantages of a soft gel.

It is an object of the present invention to provide a radiation curable gel builder composition that does not require pots, multiple brushes or tools for mixing and applying the builder nor is cleanup and sanitizing of the tools necessary. The gel coating of the present invention has superior self-leveling properties that minimize the need to shape and file the builder once it has been cured and therefore reduces discomfort to the user. The viscosity of the gel coating yields an increased level of control and precision during application of the composition to a nail eliminating the need for skilled application associated with prior art builder compositions. The radiation cure of the present invention does not exhibit any high exothermic heat spikes which could cause discomfort to the end user. In addition, the gel builder of the present invention is easily removed with a soak-off instead of extensive filing and abrasion. The low viscosity of the soft gel nail builder of the present invention enables it to be packaged in a ready to use form within a bottle or similar container that may be provided with an applicator cap having a brush. The low viscosity and self-leveling characteristics are such that the nail builder composition may be applied to a nail using the brush. After curing, the composition has a very high tensile strength yet is flexible enough not to crack. The composition has crystal clear clarity and long wear, up to 14 days.

BRIEF SUMMARY OF THE INVENTION

A radiation-curable nail gel composition for building up and extending a natural nail, the composition comprising (a) an Acrylates/Carbamate copolymer, a Urethane Dimethacrylate (UDMA) having a functional Dicarbamate group, a Isopropylidenediphenyl Bisoxyhydroxypropyl Methacrylate, and a resinous polymer containing Isophorone Diisocyanate (IPDI) end-capped with HEMA; (b) at least one mono-functional monomer; (c) a photo initiator; and (d) at least one acid-based adhesion promotor wherein the radiation curable gel composition has a viscosity in the range of about 10,000 to about 15,000 centipoise.

A UV curable gel composition adapted to be applied to a nail using a brush to build and extend it comprising one or more acrylate/carbamate copolymer resins, one or more urethane methacrylate oligomers of di-functionality, one or more methacrylate resins, one or more Isophorone Diisocyanate end-capped with Hydroxyethyl Methacrylate resins, one or more ethylenically unsaturated mono functional monomers, a photoinitiator and at least one acid-based adhesion promotor wherein the composition having a viscosity of about 11,000 centipoise to about 14,000 centipoise and a specific gravity of less than about 1.2.

A kit for applying a composition to a nail by brush to build and extend it, the kit comprising a UV curable gel composition comprising one or more acrylate/carbamate copolymer resins, one or more urethane methacrylate oligomers of di-functionality, one or more methacrylate resins, one or more Isophorone Diisocyanate end-capped with Hydroxyethyl Methacrylate resins, one or more ethylenically unsaturated mono functional monomers, at least one photoinitiator and at least one acid-based adhesion promotor wherein the composition has a viscosity of about 11,000 centipoise to about 14,000 centipoise and a specific gravity of less than about 1.2, a container or bottle adapted to substantially block the contents therein from exposure to UV light, and cap for the container or bottle, the cap having an applicator brush for applying the UV curable gel composition to a nail to build and extend it.

A method for building and extending a nail comprising the steps of providing a UV curable gel composition comprising one or more acrylate/carbamate copolymer resins, one or more urethane methacrylate oligomers of di-functionality, one or more methacrylate resins, one or more Isophorone Diisocyanate end-capped with Hydroxyethyl Methacrylate resins, one or more ethylenically unsaturated mono functional monomers, a photoinitiator and at least one acid-based adhesion promotor wherein the composition having a viscosity of about 11,000 centipoise to about 14,000 centipoise and a specific gravity of less than about 1.2, applying the composition to a nail by brushing and exposing the applied composition to UV light until cured.

DETAILED DESCRIPTION OF THE INVENTION

Oligomers for use within the scope of the present invention are Urethane Methacrylates and/or Urethane Dimethacrylates having a high percent of elongation and hardness with little to no shrinking. These oligomers may contain a carbamate functional group.

Commercially available oligomers within the scope of the present invention include, but are not limited to, Genomer 4247 UMA (Rahn), Genomer 4297 UDMA (Rahn), Genomer 4277 (Rahn), X850-0000 UDMA (Esstech), X930-0000 UDMA (Esstech), BR-551M UMA (Dymax), BR-543M UMA (Dymax), MR-4126M UMA (Metamorphic Materials), Morphomer UDMA (Metamorphic Materials), Ebecryl 4859 UDMA (Allnex), CN1969 (Sartomer) and CN1963CG UMA (Sartomer).

The above listing is not exhaustive and may include additional oligomers of varying functionality and viscosity. Low tin and ultra-low MeHQ/HQ oligomers may also be used provided they only contain BHT as the main source of inhibitor. Commercially available examples include, but are not limited to, 850-1066 UDMA w/BHT (Esstech), X850-7045 Low Tin UDMA (Esstech), and Morphomer X2-141B UDMA w/BHT(Metamorphic Materials).

The resins of the present invention are selected from the group consisting of an Acrylates/Carbamate copolymer, a Urethane Dimethacrylate (UDMA) having a functional Dicarbamate group, in addition to Isopropylidenediphenyl Bisoxyhydroxypropyl Methacrylate, and a resinous polymer containing Isophorone Diisocyanate (IPDI) end-capped with HEMA. Commercially available resins within this group include Isopropylidenediphenyl Bisoxyhydroxypropyl Methacrylate (Esstech), UDMA-IPDI (Esstech), Bis-HEMA Poly (1,4-Butanediol)-9/IPDI Copolymer (Metamorphic Materials), Bis-HEMA Poloxamer 251/IPDI Copolymer (Elementis), Bis-HEMA Poly (1,4 Butanediol)-22/IPDI Copolymer (Dymax), and Bis-HEMA Poly(1,4-Butanediol)-14/IPDI Copolymer (Guangzhou Bluesky Chemical Technology Co., Ltd.). The IPDI-containing resin is added to the oligomer complex to create the desired hardness after curing.

As noted earlier, of all the chosen resin, of particular importance are the Acrylates/Carbamate Copolymer, a Urethane Dimethacrylate with a functional Dicarbamate group, Isopropylidenediphenyl Bisoxyhydroxypropyl Methacrylate, and an Isophorone Diisocyanate (IPDI) containing Copolymer end-capped with HEMA. This set of energy curing resins, in the disclosed quantities, provide the nail "building" characteristics of the soft gel of the present invention. The Acrylates/Carbamate Copolymer component provides excellent resistance to scratching and marring to the composition post-cure. It also imparts flexibility and does not emit much heat during the cure. The Acrylates/Carbamate Copolymer component, together with the methacrylate monomer component, provides the backbone of the composition.

One of the key characteristics of the present invention is its capacity for self-leveling. The self-leveling of the energy curing liquid is mainly dependent on the surface tension. In order to achieve evenness, the surface tension must remain uniform over the entire surface. Due to the perfect flow and self-leveling of the present invention, the highest amount of transparency is also achieved. The self-leveling is attributed to the novel combination of oligomers/resin(s) chosen and the type and quantity of the chosen monomers. The composition of the present invention is also free from the inclusion of silicones/silanes, polyethylene glycols and volatile organic solvents which results in the "building" capacity of the composition. Additionally, there are no short-chain esters, alkanes and aromatic hydrocarbons in the present invention.

The preferred monomers according to the present invention are mono-functional. This prevents unwanted heat spikes that would cause pain to the end user during curing. They also function as viscosity reducing diluents. The oligomer/resin mixture before the addition of monomers should preferably exceed 100,000 centipoise at room temperature. Commercially available mono-functional monomers according to the present include, but are not limited to, 2-Hydroxyethyl Methacrylate (HEMA), Hydroxypropyl Methacrylate (HPMA), Isobornyl (Meth)Acrylate, Lauryl (Meth)Acrylate, Tetrahydrofurfuryl Methacrylate, Tridecyl Methacrylate and Stearyl Methacrylate.

The composition includes a photoinitiator. Two representative photoinitiators within the scope of the present invention are Hydroxycyclohexyl Phenyl Ketone (CPK) and Trimethylbenzoyl Diphenylphosphine Oxide (TPO). Other photoinitiators are within the scope of the present invention.

At least one acid-based adhesion promoter is necessary according to the present invention to prevent lifting of the gel after it is cured and to aid in its adhesion to the nail. Commercially available acid-based adhesion promotors include, but are not limited to X846-0000 (Esstech), CD9054 (Sartomer), Ebecryl 168 (Allnex), Genorad 40 (Rahn), and Miramer M210 (Rahn).

Additional materials that may be provided within the composition include Sucrose Benzoate, Vitamins, and a Violet Tint. Sucrose Benzoate adds high gloss and hardness characteristics together with good flexibility. Since the gel will be on the human nails for an extended period of time, vitamins may be added to nourish the nail. They may be chosen from a wide array of multipurpose vitamins. The preferred formations include Vitamin A, Vitamin E, and Pro-Vitamin B5. Lastly, it is preferable that violet dye #2 be added at a very low concentration to mask any yellowing that may occur from the combination of oligomers and monomers over time. Other pigments are within the scope of the invention. Cross-linking agents are within the scope of the present invention.

A preferred range of the ingredients for the soft gel builder according to the present invention is as follows:

| Ingredient | % Wt |
| --- | --- |
| Acrylates/Carbamate Copolymer | 30-40 |
| Urethane Dimethacrylate (UDMA) | 15-20 |
| Isopropylidenediphenyl Bisoxyhydroxypropyl Methacrylate | 5-10 |

| Ingredient | % Wt |
| --- | --- |
| Resin containing IPDI End-capped with HEMA | 5-10 |
| Isobornyl Methacrylate (IBOMA) | 15-20 |
| Hydroxypropyl Methacrylate (HPMA) | 4-8 |
| Sucrose Benzoate in Monomer Soln. | 2-4 |
| TPO | 1-2 |
| CPK | 1-2 |
| Acid-Based Adhesion Promoter | 1-2 |
| Violet #2 K7014 | <1 |
| Vitamin A Palmitate | <1 |
| Vitamin E Acetate | <1 |
| D-Panthenol | <1 |
| Total: | 100% wt |

In a preferred embodiment, the ratio of all the combined resins to all the combined monomers is about 2:1 including any in the sucrose benzoate and the adhesion promotor solutions.

The following examples, in which all parts and percentages are by weight, are presented to illustrate certain embodiments within the scope of the present invention.

The method for producing the gel builder according to the present invention is as follows. The stating materials should be weighed and mixed in a room that has UV absorber light covers so that the lighting does not cause premature polymerization. All equipment should be stainless steel rated 316 and thoroughly grounded. While the materials are not flammable, the grounding will prevent the possibility of sparking that could lead to a fire. Adequate ventilation, as well as proper Personal Protection Equipment (PPE) should be used. This may include latex or nitrile gloves, eye protection and closed toe shoes with the toes protected.

In a first phase, the resin and oligomer starting materials are warmed to approximately 40 degrees Celsius so that they become fluid. This can be achieved by placing them in a hot box with a pre-set temperature or by installing heat blankets around the drums. Care must be taken so that the temperature does not exceed 45 C. The lids of the containers should also be loosened and a bung cap removed to eliminate the buildup of pressure.

In a second phase, at the same time as the first phase or thereafter, the monomers, adhesion promoters and other ingredients can be weighed out and added to the mixing vessel. Then the photoinitiators are added and mixed with a saw tooth blade until they are completely dissolved. The violet dye and the vitamins are then added.

When the oligomers in the first phase are at the proper temperature and the second phase is ready, the oligomers are poured and weighed out one by one. These are then added one at a time to the second phase with slow to moderate mixing. The mixing speed should be controlled to prevent the incorporation of air. After the batch is uniform, the mixer should be stopped and a sample taken to the laboratory for analysis. There is no pH check. The viscosity is the critical check and should fall in the range of around 9,000 to around 12,000 centipoise initially. After 24-48 hours, the viscosity may rise but must not exceed 16,000 centipoise. The viscosity range of the final product falls into around 11,000 to around 14,000 centipoise. The product's appearance should be completely transparent (crystal clear) with a violent tint to closely match a pantone of 2715. Specific gravity shall fall into the range of 1.02-1.12.

Example 1

| Ingredient | % Wt/wt |
| --- | --- |
| Acrylates/Carbamate Copolymer | 30 |
| Urethane Dimethacrylate (UDMA) | 21 |
| Isopropylidenediphenyl Bisoxyhydroxypropyl Methacrylate | 10 |
| Resin containing IPDI End-capped with HEMA | 6 |
| Isobornyl Methacrylate (IBOMA) | 20 |
| Hydroxypropyl Methacrylate (HPMA) | 7 |
| Sucrose Benzoate in Monomer Solution | 2 |
| TPO | 2 |
| CPK | 1 |
| Acid-Based Adhesion Promoter | 0.5 |
| Violet #2 K7014 Solution | 0.2 |
| Vitamin A Palmitate | 0.1 |
| Vitamin E Acetate | 0.1 |
| D-Panthenol | 0.1 |
| Total: | 100% wt/wt |

Example 2

| Ingredient | % Wt/wt |
| --- | --- |
| Acrylates/Carbamate Copolymer | 34 |
| Urethane Dimethacrylate (UDMA) | 18 |
| Isopropylidenediphenyl Bisoxyhydroxypropyl Methacrylate | 8 |
| Resin containing IPDI End-capped with HEMA | 6 |
| Isobornyl Methacrylate (IBOMA) | 17 |
| Hydroxypropyl Methacrylate (HPMA) | 9 |
| Sucrose Benzoate in Monomer Solution | 4 |
| TPO | 2 |
| CPK | 1 |
| Acid-Based Adhesion Promoter | 0.5 |
| Violet #2 K7014 Solution | 0.2 |
| Vitamin A Palmitate | 0.1 |
| Vitamin E Acetate | 0.1 |
| D-Panthenol | 0.1 |
| Total: | 100% wt/wt |

Example 3

| Ingredient | % Wt/wt |
| --- | --- |
| Acrylates/Carbamate Copolymer | 40 |
| Urethane Dimethacrylate (UDMA) | 16 |
| Isopropylidenediphenyl Bisoxyhydroxypropyl Methacrylate | 7 |
| Resin containing IPDI End-capped with HEMA | 5 |
| Isobornyl Methacrylate (IBOMA) | 15 |
| Hydroxypropyl Methacrylate (HPMA) | 8 |
| Sucrose Benzoate in Monomer Solution | 4 |
| TPO | 2 |
| CPK | 2 |
| Acid-Based Adhesion Promoter | 0.5 |
| Violet #2 K7014 Solution | 0.2 |
| Vitamin A Palmitate | 0.1 |
| Vitamin E Acetate | 0.1 |
| D-Panthenol | 0.1 |
| Total: | 100% wt/wt |

While this invention has been described as having a preferred design, it is understood that it is capable of further modifications, uses and adaptations, both in whole and in part, while following the general principle of the invention including such departures from the present disclosure as is known or customary practice in the art to which this invention pertains, and as may be applied to the central features of this invention.

We claim:

1. A UV curable gel composition adapted to be applied by brush onto a nail to build and extend the nail, comprising:
   one or more acrylate/carbamate copolymer resins;
   one or more urethane methacrylate oligomers of di-functionality;
   one or more methacrylate resins;
   one or more Isophorone Diisocyanate end-capped with Hydroxyethyl Methacrylate groups;
   one or more ethylenically unsaturated mono functional monomers;
   at least one photoinitiator; and
   at least one acid-based adhesion promotor wherein the composition has a viscosity of about 11,000 centipoise to about 14,000 centipoise.

2. The composition of claim 1 wherein the composition has a specific gravity from about 1.02 to about 1.12.

3. The composition of claim 1 wherein the one or more acrylate/carbamate copolymer resins comprise about 30 wt. % to about 40 wt. % of the total weight of the composition, the one or more urethane methacrylate oligomers of di-functionality comprise about 15 wt. % to about 20 wt. % of the total weight of the composition, the one or more methacrylate resins comprise about 5 wt. % to about 10 wt. % of the total weight of the composition, the one or more Isophorone Diisocyanate end-capped with Hydroxyethyl Methacrylate groups comprise about 5 wt. % to about 10 wt. % of the total weight of the composition and the one or more ethylenically unsaturated mono functional monomers comprise about 20 wt. % to about 30 wt. % of the total weight of the composition.

4. The composition of claim 1 further including at least one of sucrose benzoate, vitamins, and violet dye.

5. A kit for containing and applying the UV curable gel composition for building and extending a nail of claim 1, the kit comprising a bottle adapted to block the contents therein from exposure to UV light and a bottle cap, the cap having an applicator brush for applying the UV curable gel composition to a nail.

6. A method for building and extending a nail comprising the steps of:
   a) applying the composition of claim 1 onto a nail with a brush; and
   b) exposing the applied composition to UV light to cure the applied composition.

* * * * *